US00PP13496P2

(12) United States Plant Patent
Bradford

(10) Patent No.: US PP13,496 P2
(45) Date of Patent: Jan. 21, 2003

(54) PEACH TREE NAMED 'IVORY QUEEN'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,025

(22) Filed: Dec. 13, 2001

(51) Int. Cl.[7] ..... A01H 5/00
(52) U.S. Cl. ..... Plt./195; Plt./196
(58) Field of Search ..... Plt./195, 196

(56) References Cited

U.S. PATENT DOCUMENTS

PP11,205 2/2000 Bradford ..... Plt./195

*Primary Examiner*—Bruce R. Campell
*Assistant Examiner*—W C Haas

(57) ABSTRACT

The present invention relates to a peach tree, *Prunus persica*, and more particularly to a new and distinct variety broadly characterized by a medium size, vigorous, hardy, self-fertile, productive and regular bearing tree. The fruit matures under the ecological conditions described approximately the third week in June, with first picking on Jun. 18, 2001. The fruit is uniformly medium in size, very good in flavor, globose in shape, clingstone in type, firm in texture, white in flesh color, and full red in skin color. The variety was developed as a self pollinated seedling of 'Ivory Princess' (U.S. Plant Pat. No. 11,205) white flesh peach.

1 Drawing Sheet

BOTANICAL CLASSIFICATION

*Prunus persica.*

BACKGROUND OF THE VARIETY

In a continuing effort to improve the quality of shipping fruits, I, the inventor, typically hybridize a large number of nectarine, peach, plum, apricot, and cherry seedlings each year. In an effort to exhibit recessive traits, I also grow a lesser number of open pollinated seeds of each of these fruits. The present invention relates to a new and distinct variety of peach tree, which has been denominated varietally as 'IVORY QUEEN'. The present variety was germinated by me in 1996 using embryoculture techniques in my laboratory, grown as a seedling on its own root in my greenhouse, and transplanted to a cultivated area of my experimental orchard at Bradford Farms near Le Grand, Calif. in Merced County (San Joaquin Valley). It ws developed as a self pollinated seedling of 'Ivory Princess' (U.S. Plant Pat. No. 11,205) white flesh peach. Subsequent to origination of the present variety of peach tree, I assexually reproduced it by budding and grafting in the experimental orchard described above, and such reproduction of plant and fruit characteristics were true to the original plant in all respects. The reproduction of the variety included the use of 'Nemaguard'. Rootstock (unpatented) upon which the present variety was compatible and true to type.

The present variety is similar to its parent, 'Ivory Princess' (U.S. Plant Pat. No. 11,205) peach, by producing white flesh clingstone peaches that are globose in shape, firm in texture, and mostly red in skin color, but is distinguished therefrom and an improvement thereon by producing fruit that matures about 10 days later.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 23, 2001, on the original tree during its fifth growing season. All major color code designations are by reference to the Inter-Society Color Council, National Bureau of Standards. Common color names are also used occasionally.

TREE

Size: Medium, reaching and maintaining a height of 13' [3.96 m.] after five growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Upright and dense.
Form: Vase formed.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Trunk:
*Size.*—Medium, reaching a maximum diameter of 4" [102 mm.] after the fifth growing season.

*Texture.*—Rough.
*Bark color.*—Grayish brown [61. gy.Br].
*Lenticels.*—Numerous. Color: Dark orange yellow [72. d.OY]. Average Size: 5/16" [7.9 mm.].

Branches:
*Size.*—Diameter of scaffold is 2" [51 mm.] measured 12" above the crotch, typical of *Prunus persica*, and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Strong yellow green [117. s. YG]. Older Wood: Moderate brown [58. m.Br].
*Lenticels.*—Numerous. Color: Light yellowish brown [76. l.yBr]. Typical Size: 1/16" to 1/14" [1.16–6.4 mm.].

Leaves:
*Size.*—Large. Average Length: 6½" [165 mm.]. Average Width: 1 7/16" [36.5 mm.].
*Arrangement.*—Alternate.
*Thickness.*—Medium.
*Form.*—Elliptical.
*Apex.*—Acuminate.
*Base.*—Acute with an average angle of 50 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ½" [12.7 mm.]. Average Thickness: 1/16" [1.6 mm.]. Color: Moderate yellow green [120. m.YG].
*Stipules.*—Numerous, up to 2 per leaf and 6 per growing tip. Average Length: ⅜" [9.5 mm.]. Color: Moderate yellow green [120. m.YG] becoming Dark brown [59. d.Br] with age.
*Glands.*—Number: 2 to 5. Position: Mostly alternate, positioned both on the petiole and the base of blade. Size: Medium. Form: Mature glands are reniform, but have a globose shape when very small and immature. Color: Brilliant yellow green [116. brill.YG].
*Leaf buds.*—Pointed.

Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Not appressed.
*Surface.*—Pubescent.
*Color.*—Moderate purplish pink [250. m.pPk].

Flowers: Perfect, complete, perigynous, usually a single pistil, typically thirty or more stamens, five sepals and petal locations alternately positioned.
*Type.*—Showy.
*Average flower diameter.*—1¾" [44.5 mm.].
*Number of petals.*—Usually five.
*Petal shape.*—Circular.
*Petal margin.*—Slightly wavy.
*Average petal diameter.*—11/16" [17.5 mm.].
*Average petal length.*—11/16" [17.5 mm.].
*Petal apex.*—Rounded.
*Petal base.*—Rounded, slightly wavy.
*Petal color.*—Pale purplish pink [252. p.pPk].
*Anther color.*—Dark red [16. d.R] when first open.
*Stigma color.*—Moderate yellow [87. m.Y].
*Sepal color.*—Grayish purplish red [262. gy.pR].
*Sepal length.*—3/16" [4.8 mm].
*Sepal width.*—3/16" [4.8 mm].
*Average pistil length.*—⅝" [15.9 mm.].
*Average stamen length.*—⅝" [15.9 mm.].
*Fragrance.*—Moderate when nectar is present.
*Blooming period.*—Late compared with other varieties.
*Onset of bloom.*—One percent on Mar. 3, 2001.
*Duration of bloom.*—One to two weeks, dependent on ambient temperature.
*Number per cluster.*—Usually 1, rarely more than 2.

FRUIT

Maturity when described: Firm ripe, Jun. 23, 2001.
Date of first picking: Jun. 18, 2001.
Date of last picking: Jul. 28, 2001.
Size: Uniform, medium.
*Average diameter axially.*—2⅝" [66.7 mm.].
*Average diameter across suture plane.*—2¾" [69.9 mm.].
*Typical weight.*—6.63 ounces [188 grams].

Form: Uniform, mostly symmetrical, globose with slight axial compression.
*Longitudinal section form.*—Roundish, flattened toward the poles.
*Transverse section through diameter.*—Roundish.

Suture: An inconspicuous line extending from the base to the pistil point with some shallow grooving toward the apex.
Ventral surface: Rounded, slightly lipped toward the apex.
Lips: Slightly unequal.
Cavity: Flaring, circular, suture showing on one side, Yellowish white [92. yWhite] stem markings typical.
*Depth.*—½" [12.7 mm.].
*Breadth.*—1" [25.4 mm.].
Base: Truncate, somewhat cuneate when viewed parallel to the suture.
Apex: Rounded.
Pistil point: Apical, 1/16" [1.6 mm.] in length, usually depressed within the suture.
Stem: Short.
*Average length.*—5/16" [7.9 mm.].
*Average width.*—3/16" [4.8 mm.].

Skin:
*Thickness.*—Medium.
*Surface.*—Pubescent.
*Tenacity.*—Tenacious to flesh.
*Astringency.*—Nonastringent.
*Tendency to crack.*—None observed.
*Color.*—Very dark red [17. v.d.R] smoothly blending into Moderate red [15. m.R].

Down: Moderate, short, very difficult to roll up when rubbed.

Flesh:
*Color.*—Yellowish white [92. yWhite] with very slight Deep pink [3. deep Pk] flecking close to the skin.
*Surface of pit cavity.*—Deep pink [3. deep Pk] and Yellowish white [92. yWhite] fibers breaking when twisted from the stone.
*Amygdalin.*—Scarce.
*Juice.*—Moderate, rich.
*Texture.*—Firm, crisp.
*Fibers.*—Abundant, fine.

*Ripens.*—Slightly earliest toward the apex.
*Flavor.*—Subacidic and sweet, ranging from 14 to 15 brix.
*Aroma.*—Slight.
*Eating quality.*—Very good.

STONE

Type: Clingstone.
Form: Oval.
Base: Straight.
Apex: Acute, forming an angle of 90 degrees with a protruding tip ⅛" [3.2 mm.] long.
Sides: Equal.
Surface: Irregularly furrowed near the apex and pitted toward the base.
Ridges: Jagged toward the base.
Color: Light yellowish brown [76. l.y.Br].
Average pit wall thickness.—¼" [6.4 mm.].
Average width: 1 1/16" [27.0 mm.].
Average length: 1¼" [31.8 mm.].
Tendency to split: Slight in wet season.
Kernel:
*Form.*—Oval.
*Color.*—Brilliant yellow [83. brill.Y] with pronounced Deep yellowish brown [75. deep yBr] veins.
*Taste.*—Very bitter.
*Viable.*—Yes.
*Average width.*—7/16" [11.1 mm.].
*Average length.*—11/16" [17.5 mm.].
*Pellicle color.*—Deep brown [56. deep Br].
*Amygdalin.*—Abundant.

USE

Market: Fresh and long distance shipping.
Keeping quality: Fruit quality observed to remain in good condition in excess of 17 days in standard cold room at 36° Fahrenheit [2° Celsius].
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its parent, 'Ivory Princess' (U.S. Plant Pat. No. 11,205) peach, by producing white flesh clingstone peaches that are globose in shape, firm in texture, and mostly red in skin color, but is distinguished therefrom and an improvement thereon by producing fruit that matures about 10 days later.

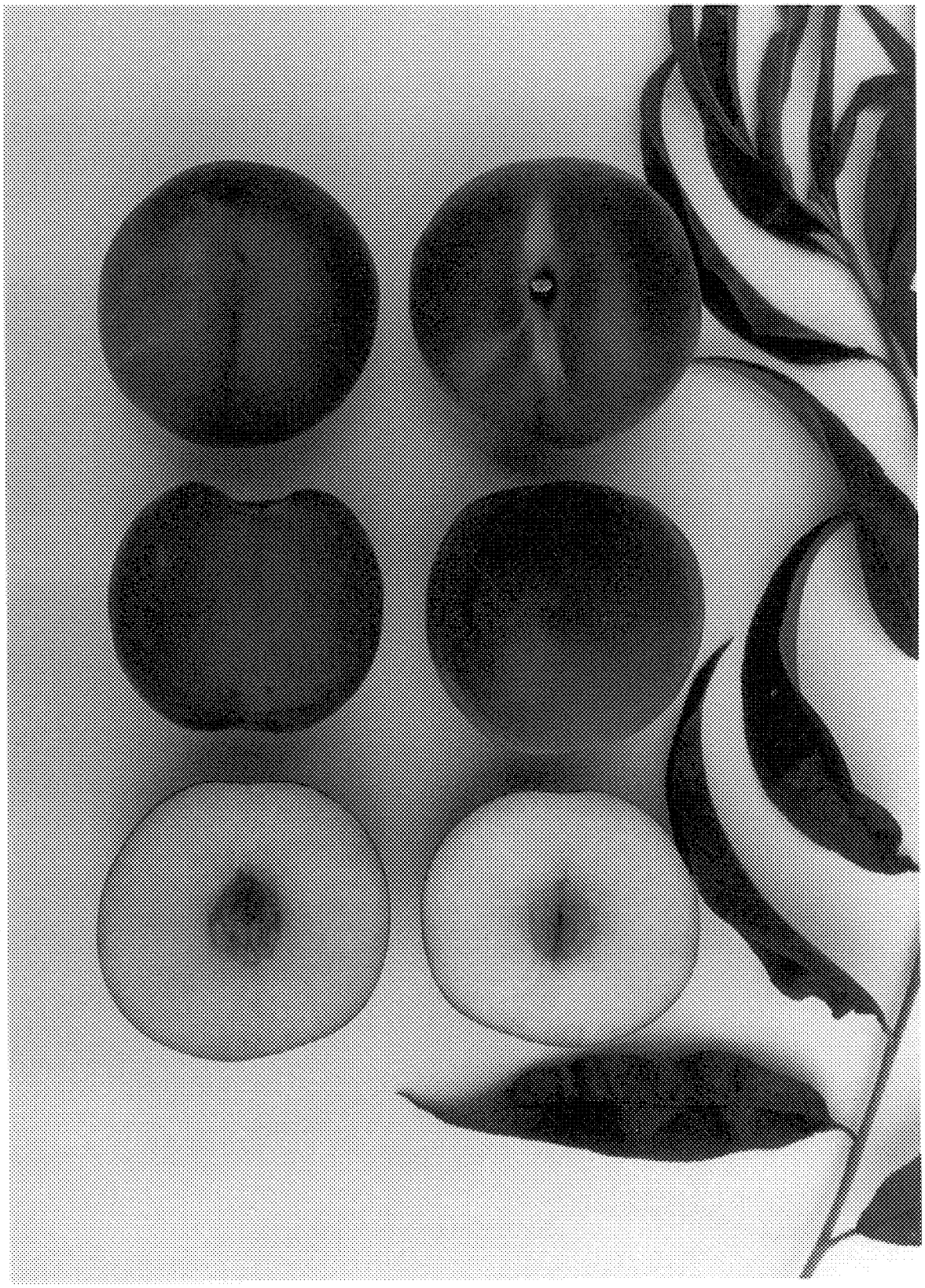

* * * * *